United States Patent
Nyikos et al.

(10) Patent No.: US 12,383,725 B2
(45) Date of Patent: *Aug. 12, 2025

(54) BEARINGLESS IMPLANTABLE BLOOD PUMP

(71) Applicant: TC1 LLC, St. Paul, MN (US)

(72) Inventors: Thomas Nyikos, Zurich (CH); Bernhard Warberger, Zurich (CH)

(73) Assignee: TC1 LLC, St. Paul, MN (US)

( * ) Notice: Subject to any disclaimer, the term of this patent is extended or adjusted under 35 U.S.C. 154(b) by 611 days.

This patent is subject to a terminal disclaimer.

(21) Appl. No.: 17/205,336

(22) Filed: Mar. 18, 2021

(65) Prior Publication Data
US 2021/0205600 A1 Jul. 8, 2021

Related U.S. Application Data

(63) Continuation of application No. 16/204,015, filed on Nov. 29, 2018, now Pat. No. 10,973,967.

(60) Provisional application No. 62/615,708, filed on Jan. 10, 2018.

(51) Int. Cl.
| | | |
|---|---|---|
| *A61M 60/422* | (2021.01) | |
| *A61M 60/148* | (2021.01) | |
| *A61M 60/178* | (2021.01) | |
| *A61M 60/216* | (2021.01) | |
| *A61M 60/538* | (2021.01) | |

(Continued)

(52) U.S. Cl.
CPC ........ *A61M 60/422* (2021.01); *A61M 60/148* (2021.01); *A61M 60/178* (2021.01); *A61M 60/216* (2021.01); *A61M 60/538* (2021.01); *A61M 60/81* (2021.01); *A61M 60/857* (2021.01)

(58) Field of Classification Search
CPC .. A61M 60/422; A61M 60/81; A61M 60/538; A61M 60/148; A61M 60/178; A61M 60/857; A61M 60/216
See application file for complete search history.

(56) References Cited

U.S. PATENT DOCUMENTS

| | | |
|---|---|---|
| 845,816 A | 3/1907 | Prindle |
| 888,654 A | 5/1908 | Prindle |
| 1,026,101 A | 5/1912 | Marsh |

(Continued)

FOREIGN PATENT DOCUMENTS

| | | |
|---|---|---|
| CN | 300837668 | 10/2008 |
| EP | 150320 | 5/1990 |

(Continued)

OTHER PUBLICATIONS

Antaki et al., "PediaFlowTM Maglev Ventricular Assist Device: A Prescriptive Design Approach", Cardiovascular Engineering and Technology, vol. 1, No. 1, Mar. 2010, pp. 104-121.

(Continued)

*Primary Examiner* — Michael J Lau
(74) *Attorney, Agent, or Firm* — Kilpatrick Townsend & Stockton LLP (57) ABSTRACT

Implantable blood pumps and related methods employ a compact rotary motor. The compact rotary motor includes a stator and a rotor. The stator is disposed within a housing circumferentially about a dividing wall such that a blood flow conduit extends through the stator. The stator is disposed circumferentially around at least a portion of the rotor.

21 Claims, 7 Drawing Sheets

(51) Int. Cl.
*A61M 60/81* (2021.01)
*A61M 60/857* (2021.01)

(56) References Cited

U.S. PATENT DOCUMENTS

| | | | |
|---|---|---|---|
| 2,128,988 A | 9/1938 | Russell |
| 2,747,512 A | 5/1956 | Paul |
| 2,864,552 A | 12/1958 | Norman |
| 3,005,117 A | 10/1961 | Buchhold |
| 3,066,849 A | 12/1962 | Beams |
| 3,122,101 A | 2/1964 | Baker et al. |
| 3,225,608 A | 12/1965 | Ivan |
| 3,401,640 A | 9/1968 | John et al. |
| 3,499,274 A | 3/1970 | Fergason |
| 3,575,536 A | 4/1971 | Jacobs et al. |
| 3,597,022 A | 8/1971 | Waldron |
| 3,608,088 A | 9/1971 | Dorman et al. |
| 3,611,815 A | 10/1971 | Fischell |
| 3,647,324 A | 3/1972 | Rafferty et al. |
| 3,650,581 A | 3/1972 | Boden et al. |
| 3,938,913 A | 2/1976 | Isenberg et al. |
| 3,957,389 A | 5/1976 | Rafferty et al. |
| 4,082,376 A | 4/1978 | Wehde et al. |
| 4,135,253 A | 1/1979 | Reich et al. |
| 4,213,207 A | 7/1980 | Wilson |
| 4,340,260 A | 7/1982 | Forster et al. |
| 4,382,199 A | 5/1983 | Isaacson |
| 4,398,773 A | 8/1983 | Boden et al. |
| 4,405,286 A | 9/1983 | Studer |
| 4,408,966 A | 10/1983 | Maruyama |
| 4,475,866 A | 10/1984 | Kambe et al. |
| 4,507,048 A | 3/1985 | Belenger et al. |
| 4,589,822 A | 5/1986 | Clausen et al. |
| 4,642,036 A | 2/1987 | Young |
| 4,688,998 A | 8/1987 | Olsen et al. |
| 4,704,121 A | 11/1987 | Moise |
| 4,763,032 A | 8/1988 | Bramm et al. |
| 4,779,614 A | 10/1988 | Moise |
| 4,844,707 A | 7/1989 | Kletschka |
| 4,876,492 A | 10/1989 | Lester et al. |
| 4,878,831 A | 11/1989 | Ewing |
| 4,929,158 A | 5/1990 | Girault |
| 4,944,748 A | 7/1990 | Bramm et al. |
| 4,957,504 A | 9/1990 | Chardack |
| 5,044,897 A * | 9/1991 | Dorman ............ A61M 60/824 417/365 |
| 5,055,005 A | 10/1991 | Kletschka |
| 5,078,741 A | 1/1992 | Bramm et al. |
| 5,079,467 A | 1/1992 | Dorman |
| 5,098,256 A | 3/1992 | Smith |
| 5,106,273 A | 4/1992 | Lemarquand et al. |
| 5,112,200 A | 5/1992 | Isaacson et al. |
| 5,112,202 A | 5/1992 | Oshima et al. |
| 5,126,612 A | 6/1992 | Girault |
| 5,127,792 A | 7/1992 | Katsuta et al. |
| 5,159,219 A | 10/1992 | Chu et al. |
| 5,177,387 A | 1/1993 | Mcmichael et al. |
| 5,195,877 A | 3/1993 | Kletschka |
| 5,220,232 A | 6/1993 | Rigney, II et al. |
| 5,341,059 A | 8/1994 | Fukuyama et al. |
| 5,360,317 A | 11/1994 | Clausen et al. |
| 5,385,581 A | 1/1995 | Bramm et al. |
| 5,470,208 A | 11/1995 | Kletschka |
| 5,678,306 A | 10/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,798,454 A | 8/1998 | Nakazeki et al. |
| 5,808,437 A | 9/1998 | Schob |
| 5,888,242 A | 3/1999 | Antaki et al. |
| 5,917,297 A | 6/1999 | Gerster et al. |
| 5,928,131 A | 7/1999 | Prem |
| 5,947,703 A | 9/1999 | Nojiri et al. |
| 6,053,705 A | 4/2000 | Schob et al. |
| 6,071,093 A | 6/2000 | Hart |
| 6,100,618 A | 8/2000 | Schoeb et al. |
| 6,116,862 A | 9/2000 | Rau et al. |
| 6,130,494 A | 10/2000 | Schob |
| 6,146,325 A | 11/2000 | Lewis et al. |
| 6,186,665 B1 | 2/2001 | Maher et al. |
| 6,222,290 B1 | 4/2001 | Schoeb et al. |
| 6,227,797 B1 | 5/2001 | Watterson et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schob |
| 6,293,901 B1 | 9/2001 | Prem |
| 6,302,661 B1 | 10/2001 | Khanwilkar et al. |
| 6,351,048 B1 | 2/2002 | Schob et al. |
| 6,355,998 B1 | 3/2002 | Schoeb et al. |
| 6,394,769 B1 | 5/2002 | Beamson et al. |
| 6,447,266 B2 | 9/2002 | Antaki et al. |
| 6,468,041 B2 | 10/2002 | Ozaki |
| 6,547,530 B2 | 4/2003 | Ozaki et al. |
| 6,559,567 B2 | 5/2003 | Schoeb |
| 6,575,717 B2 | 6/2003 | Ozaki et al. |
| 6,589,030 B2 | 7/2003 | Ozaki |
| 6,605,032 B2 | 8/2003 | Benkowski et al. |
| 6,623,475 B1 | 9/2003 | Siess |
| 6,626,644 B2 | 9/2003 | Ozaki |
| 6,634,224 B1 | 10/2003 | Schob et al. |
| 6,640,617 B2 | 11/2003 | Schob et al. |
| 6,641,378 B2 | 11/2003 | Davis et al. |
| 6,688,861 B2 | 2/2004 | Wampler |
| 6,707,200 B2 | 3/2004 | Carroll et al. |
| 6,711,943 B1 | 3/2004 | Schob |
| 6,817,836 B2 | 11/2004 | Nose et al. |
| 6,949,066 B2 | 9/2005 | Beamson et al. |
| 6,991,595 B2 | 1/2006 | Burke et al. |
| 7,070,398 B2 | 7/2006 | Olsen et al. |
| 7,112,903 B1 | 9/2006 | Schob |
| 7,138,776 B1 | 11/2006 | Gauthier et al. |
| 7,150,711 B2 | 12/2006 | Nusser et al. |
| D534,548 S | 1/2007 | Urano et al. |
| 7,160,242 B2 | 1/2007 | Yanai |
| 7,229,258 B2 | 6/2007 | Wood et al. |
| 7,229,474 B2 | 6/2007 | Hoffmann et al. |
| 7,239,098 B2 | 7/2007 | Masino |
| 7,284,956 B2 | 10/2007 | Nose et al. |
| 7,338,521 B2 | 3/2008 | Antaki et al. |
| 7,462,019 B1 | 12/2008 | Allarie et al. |
| 7,497,116 B2 | 3/2009 | Miyakoshi et al. |
| 7,511,443 B2 | 3/2009 | Townsend et al. |
| 7,578,782 B2 | 8/2009 | Miles et al. |
| 7,591,777 B2 | 9/2009 | LaRose |
| 7,645,225 B2 | 1/2010 | Medvedev et al. |
| 7,699,586 B2 | 4/2010 | LaRose et al. |
| 7,699,588 B2 | 4/2010 | Mendler |
| 7,854,631 B2 | 12/2010 | Townsendl et al. |
| 7,861,582 B2 | 1/2011 | Miyakoshi et al. |
| 7,887,479 B2 | 2/2011 | LaRose et al. |
| 7,893,644 B2 | 2/2011 | Townsend et al. |
| 7,951,062 B2 | 5/2011 | Morello |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,157,720 B2 | 4/2012 | Marseille et al. |
| 8,303,482 B2 | 11/2012 | Schima et al. |
| 8,323,174 B2 | 12/2012 | Jeevanandam et al. |
| 8,382,830 B2 | 2/2013 | Maher et al. |
| 8,419,609 B2 | 4/2013 | Laorse et al. |
| 8,449,444 B2 | 5/2013 | Poirier |
| 8,506,470 B2 | 8/2013 | LaRose et al. |
| 8,506,471 B2 | 8/2013 | Bourque |
| 8,517,699 B2 | 8/2013 | Horvath |
| 8,556,795 B2 | 10/2013 | Bolyard et al. |
| 8,562,508 B2 | 10/2013 | Dague et al. |
| 8,581,462 B2 | 11/2013 | Nussbaumer |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,764,621 B2 | 7/2014 | Badstibner et al. |

(56) References Cited

U.S. PATENT DOCUMENTS

| | | | |
|---|---|---|---|
| 8,852,072 B2 | 10/2014 | White et al. |
| 8,864,643 B2 | 10/2014 | Reichenbach et al. |
| 8,870,739 B2 | 10/2014 | LaRose et al. |
| 8,882,477 B2 | 11/2014 | Fritz, IV et al. |
| 8,882,744 B2 | 11/2014 | Dormanen et al. |
| 8,956,275 B2 | 2/2015 | Bolyard et al. |
| 9,068,572 B2 | 6/2015 | Ozaki et al. |
| 9,079,043 B2 | 7/2015 | Stark et al. |
| 9,091,271 B2 | 7/2015 | Bourque |
| 9,091,272 B2 | 7/2015 | Kim et al. |
| 9,265,870 B2 | 2/2016 | Reichenbach et al. |
| 9,382,908 B2 | 7/2016 | Ozaki et al. |
| 9,427,510 B2 * | 8/2016 | Siebenhaar | A61M 60/178 |
| 9,492,599 B2 * | 11/2016 | Schimpf | H05K 3/303 |
| 9,675,741 B2 | 6/2017 | Bourque |
| 10,973,967 B2 * | 4/2021 | Nyikos | A61M 60/81 |
| 2002/0105241 A1 | 8/2002 | Carroll et al. |
| 2003/0021683 A1 | 1/2003 | Capone et al. |
| 2004/0236420 A1 | 11/2004 | Yamane et al. |
| 2005/0004421 A1 | 1/2005 | Pacella et al. |
| 2005/0025630 A1 | 2/2005 | Ayre et al. |
| 2005/0071001 A1 | 3/2005 | Jarvik |
| 2005/0135948 A1 | 6/2005 | Olsen et al. |
| 2005/0147512 A1 | 7/2005 | Chen et al. |
| 2006/0122456 A1 * | 6/2006 | LaRose | A61M 60/237 |
| | | | 600/16 |
| 2007/0100196 A1 * | 5/2007 | LaRose | A61M 60/81 |
| | | | 600/16 |
| 2009/0064755 A1 | 3/2009 | Fleischli et al. |
| 2009/0234447 A1 | 9/2009 | Larose et al. |
| 2010/0130809 A1 | 5/2010 | Morello |
| 2010/0150749 A1 | 6/2010 | Horvath |
| 2010/0152526 A1 | 6/2010 | Pacella et al. |
| 2010/0241223 A1 | 9/2010 | Lee et al. |
| 2010/0327687 A1 | 12/2010 | Iannello et al. |
| 2011/0002794 A1 | 1/2011 | Haefliger et al. |
| 2011/0031836 A1 | 2/2011 | Nussbaumer |
| 2011/0054239 A1 | 3/2011 | Sutton et al. |
| 2011/0071337 A1 | 3/2011 | Thompson et al. |
| 2011/0144413 A1 * | 6/2011 | Foster | A61M 60/226 |
| | | | 600/16 |
| 2011/0187217 A1 | 8/2011 | Nussbaumer |
| 2011/0237863 A1 | 9/2011 | Ricci et al. |
| 2011/0245582 A1 | 10/2011 | Zafirelis et al. |
| 2011/0313237 A1 | 12/2011 | Miyakoshi et al. |
| 2012/0035411 A1 | 2/2012 | LaRose et al. |
| 2012/0046514 A1 * | 2/2012 | Bourque | A61M 60/515 |
| | | | 600/16 |
| 2012/0059212 A1 | 3/2012 | LaRose et al. |
| 2012/0134832 A1 | 5/2012 | Wu |
| 2012/0226097 A1 | 9/2012 | Smith et al. |
| 2012/0245680 A1 | 9/2012 | Masuzawa et al. |
| 2012/0245681 A1 | 9/2012 | Casas et al. |
| 2012/0253103 A1 | 10/2012 | Robert |
| 2012/0310036 A1 | 12/2012 | Peters et al. |
| 2013/0164161 A1 * | 6/2013 | Schob | H02K 1/06 |
| | | | 417/420 |
| 2013/0314047 A1 | 11/2013 | Eagle et al. |
| 2013/0331934 A1 | 12/2013 | Kabir et al. |
| 2013/0345492 A1 | 12/2013 | Pfeffer et al. |
| 2014/0030122 A1 | 1/2014 | Ozaki et al. |
| 2014/0062239 A1 * | 3/2014 | Schoeb | A61M 60/538 |
| | | | 310/90.5 |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0303426 A1 | 10/2014 | Kerkhoffs et al. |
| 2014/0357937 A1 | 12/2014 | Reyes et al. |
| 2014/0364768 A1 | 12/2014 | Hastie et al. |
| 2015/0051438 A1 | 2/2015 | Taskin |
| 2015/0151031 A1 | 6/2015 | Yaghdjian |
| 2015/0211542 A1 | 7/2015 | Scheckel |
| 2015/0273125 A1 | 10/2015 | Bourque |
| 2015/0294550 A1 * | 10/2015 | Kimball | A61M 60/538 |
| | | | 340/636.1 |
| 2016/0331881 A1 | 11/2016 | Siebenhaar et al. |
| 2017/0119946 A1 | 5/2017 | Mcchrystal et al. |
| 2017/0246365 A1 | 8/2017 | Bourque |
| 2017/0302145 A1 | 10/2017 | Holenstein et al. |

FOREIGN PATENT DOCUMENTS

| | | |
|---|---|---|
| EP | 60569 | 12/1990 |
| EP | 378251 | 6/1994 |
| EP | 2357374 | 8/2011 |
| GB | 1491710 | 11/1977 |
| JP | 01257792 | 10/1989 |
| JP | 02016390 | 1/1990 |
| JP | 03088996 | 4/1991 |
| JP | 04148095 | 5/1992 |
| JP | 2000510929 | 8/2000 |
| JP | 2002512333 | 4/2002 |
| JP | 2003093500 | 4/2003 |
| JP | 2011530315 | 12/2011 |
| WO | 9953974 | 10/1999 |
| WO | 2004098677 | 11/2004 |
| WO | 2005032620 | 4/2005 |
| WO | 2006137496 | 12/2006 |
| WO | 2010015836 | 2/2010 |
| WO | 2010023815 | 3/2010 |
| WO | 2010036815 | 4/2010 |
| WO | 2012028181 | 3/2012 |

OTHER PUBLICATIONS

Barletta et al., "Design of a Bearing Less Blood Pump", Proc. Third International Symposium on Magnetic Suspension Technology, Jul. 1, 1996, pp. 265-274.

Izraelev et al., "A Passively-Suspended Tesla Pump Left Ventricular Assist Device", NIH Public Access, vol. 55, No. 6, 2009, pp. 556-561.

Steinert et al., "Concept of a 150 krpm Bearingless Slotless Disc Drive with Combined Windings", Proceedings of the IEEE International Electric Machines and Drives Conference (IEMDC 2013), 2013, pp. 311-318.

Steinert et al., "Slotless Bearingless Disk Drive for High-Speed and High-Purity Applications", IEEE Transactions on Industrial Electronics, vol. 61, No. 11, Nov. 2014, pp. 975-981.

Steinert et al., "Topology Evaluation of Slotless Bearingless Motors with Toroidal Windings", The 2014 International Power Electronics Conference, 2014, pp. 974-981.

* cited by examiner

BEARINGLESS IMPLANTABLE BLOOD PUMP

CROSS REFERENCE TO RELATED APPLICATIONS

The present application is a Continuation of U.S. patent application Ser. No. 16/204,015, now U.S. Pat. No. 10,973,967, filed Nov. 29, 2018 (Allowed); which claims the benefit of U.S. application No. 62/615,708 filed Jan. 10, 2018, the full disclosures which are incorporated herein by reference in their entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In many embodiments, an implantable blood pump includes a rotary motor that includes a compact stator assembly. The compact size of the stator assembly is enabled by the stator assembly including a compact stator core, which includes a toroidal portion, and stator coils. Each of the stator coils extend around a respective separated segment of the toroidal portion. In many embodiments, the stator does not extend beyond a disk-shaped volume having a compact thickness (e.g., less than 1.0 inches) in a direction parallel to the axis of rotation of the rotary motor), thereby enabling the stator assembly to have a corresponding compact thickness parallel to the axis of rotation of the rotary motor. In some embodiments, the stator core includes separated stator teeth that extend inwardly from the toroidal portion between adjacent pairs of the stator coils. In some embodiments, the rotary motor includes rotor position sensors (e.g., hall effect sensors). Each of the rotor position sensors can be disposed in or adjacent to a respective gap between adjacent pairs of the stator coils. The compact size of the stator assembly parallel to the axis of rotation of the rotary motor enables the implantable blood pump to have a compact size parallel to the axis of rotation of the rotary motor, thereby requiring less space within the thoracic cavity.

Thus, in one aspect, a first implantable blood pump includes a housing and a rotary motor. The housing defines an inlet opening, an outlet opening, and a dividing wall within the housing defining a blood flow conduit. The blood flow conduit extends between the inlet opening and the outlet opening. The rotary motor includes a stator and a rotor. The stator includes a stator core and stator coils. The stator core includes a toroidal portion and stator teeth. Each of the stator teeth extend toward the rotor from the toroidal portion. Each of the stator teeth is separated from each of an adjacent two of the stator teeth by a respective adjacent intervening segment of the toroidal portion. Each of the stator coils extends around one of the intervening segments of the toroidal portion. The stator is disposed within the housing circumferentially about the dividing wall such that the blood flow conduit extends through the stator core. The stator core is disposed circumferentially around at least a portion of the rotor. The rotor has a rotor axis of rotation and includes a rotor magnet for driving the rotor. The stator teeth axially overlap the rotor magnet with respect to the rotor axis of rotation. In many embodiments, the stator does not extend beyond a disk-shaped volume having a compact thickness (e.g., less than 1.0 inches) in a direction parallel to the rotor axis of rotation.

In many embodiments, the first implantable blood pump is configured to pump blood from a heart ventricle to the aorta. In some embodiments, the outlet opening is oriented at an angle relative to the input opening. The inlet opening can be oriented to receive blood directly from a heart ventricle and the output opening oriented to output blood in a direction transverse to the orientation of the inlet opening so as to reduce the length of a blood flow cannula used to transfer the blood flow from the output opening to the aorta. The rotor can include centrifugal pump impeller blades.

In many embodiments of the first implantable blood pump, the rotor defines a rotor blood flow conduit that extends through the stator. For example, in many embodiments, the rotor defines a rotor blood flow conduit that extends through the rotor, thereby extending through the stator.

The rotor can have any suitable number of magnetic moments. In some embodiments, the rotor has only one magnetic moment.

In some embodiments, the first implantable blood pump includes one or more rotor position sensors that generate output indicative of the orientation of the rotor for use in electronic commutation of the rotary motor. In some embodiments, the output of the one or more rotor position sensors is indicative of the position of the rotor within the blood flow conduit transverse to the rotor axis of rotation (e.g., in two different directions transverse to the rotor axis of rotation). In some embodiments, the position of the rotor within the blood flow conduit transverse to the rotor axis of rotation is used to control operation of the stator to control magnetic levitation of the rotor within the blood flow conduit. In some embodiments, the one or more rotor position sensors includes hall effect sensors. In some embodiments, each of the hall effect sensors is disposed in or adjacent to a respective gap between an adjacent pair of the stator coils. In some embodiments, each of the hall effect sensors is disposed aligned with and above or below a respective gap between an adjacent pair of the stator coils.

In some embodiments, the first implantable blood pump includes control electronics disposed within the housing. In such embodiments, the control electronics can be configured to control current passing through each of the stator coils to radially levitate the rotor and rotate the rotor within the blood flow conduit.

In many embodiments of the first implantable blood pump, an axial position of the rotor along the blood flow conduit is restrained via passive magnetic interaction between the rotor and the stator such that the stator functions as a passive magnetic bearing that controls the axial position of the rotor parallel to the rotor axis of rotation. In such embodiments, the first implantable blood pump can be configured without dedicated magnetic axial bearings that restrain the axial position of the rotor along the blood flow conduit.

In many embodiments of the first implantable blood pump, the rotor is separated from the dividing wall so as to accommodate flow of blood around the rotor. For example, in some embodiments of the first implantable blood pump, a gap between the rotor and the dividing wall is between about 0.2 mm to about 2 mm with the rotor centered relative to the stator core. A gap between the rotor and at least one of the stator teeth can be between about 0.3 mm to about 2.4 mm with the rotor centered relative to the stator core.

In another aspect, a second implantable blood pump includes a housing and a rotary motor. The housing defines an inlet opening, an outlet opening, and a dividing wall defining a blood flow conduit extending from the inlet opening to the outlet opening. The rotary motor includes a stator, hall effect sensors, and a rotor. The stator includes a stator core and stator coils. The stator core includes a toroidal portion. Each of the stator coils extends around one of separated segments of the toroidal portion. The stator is disposed within the housing circumferentially about the dividing wall such that the blood flow conduit extends through the stator core. The stator core is disposed circumferentially around at least a portion of the rotor. Each of the hall effect sensors is disposed in a respective gap between an adjacent pair of the stator coils. The rotor has a rotor axis of rotation and includes a rotor magnet for driving the rotor. The stator core axially overlaps with the rotor magnet with respect to the rotor axis of rotation. In many embodiments, the stator does not extend beyond a disk-shaped volume having a compact thickness (e.g., less than 1.0 inches) in a direction parallel to the rotor axis of rotation.

In many embodiments, the second implantable blood pump is configured to pump blood from a heart ventricle to the aorta. In some embodiments, the outlet opening is oriented at an angle relative to the input opening. The inlet opening can be oriented to receive blood directly from a heart ventricle and the output opening oriented to output blood in a direction transverse to the orientation of the inlet opening so as to reduce the length of a blood flow cannula used to transfer the blood flow from the output opening to the aorta. The rotor can include centrifugal pump impeller blades.

In many embodiments of the second implantable blood pump, the rotor defines a rotor blood flow conduit that extends through the stator. For example, in many embodiments, the rotor defines a rotor blood flow conduit that extends through the rotor, thereby extending through the stator.

The rotor can have any suitable number of magnetic moments. In some embodiments, the rotor has only one magnetic moment.

In some embodiments, the second implantable blood pump includes control electronics disposed within the housing. In such embodiments, the control electronics can be configured to control current passing through each of the stator coils to radially levitate the rotor and rotate the rotor within the blood flow conduit.

In many embodiments of the second implantable blood pump, an axial position of the rotor along the blood flow conduit is restrained via passive magnetic interaction between the rotor and the stator. In such embodiments, the second implantable blood pump can be configured without dedicated magnetic axial bearings that restrain the axial position of the rotor along the blood flow conduit.

In many embodiments of the second implantable blood pump, the rotor is separated from the dividing wall so as to accommodate flow of blood around the rotor. For example, in some embodiments of the second implantable blood pump, a gap between the rotor and the dividing wall is between about 0.2 mm to about 2 mm with the rotor centered relative to the stator core. A gap between the rotor and at least one of the stator coils can be between about 0.3 mm to about 2.4 mm with the rotor centered relative to the stator core.

In another aspect, a method of assisting blood circulation in a patient is provided. The method includes drawing a flow of blood from a patient's heart into a blood flow channel formed by a housing via rotation of a rotor comprising impeller blades. The flow of blood is passed through a toroidal portion of a motor stator core. Delivery of current to each of a plurality of stator coils is controlled to control a radial position of the rotor within the blood flow channel and to control rotation of the rotor within the blood flow channel. The rotor is rotated around a rotor axis of rotation. Each of the stator coils extends around one of separated segments of the toroidal portion. The rotor has permanent magnetic poles for magnetic levitation and rotation of the rotor. The flow of blood is output from the blood flow channel to the patient.

In many embodiments, the method further includes processing output from a plurality of hall sensors to determine an orientation of the rotor. Each of the hall effect sensors can be disposed in a respective gap between an adjacent pair of the stator coils.

In many embodiments, the method further includes supporting control electronics within the housing and between the stator core and the patient's heart. The control electronics can control the delivery of current to each of the stator coils.

In many embodiments, the method further includes flowing blood through and around the rotor. For example, the method can include (a) passing a first portion of the flow of blood through a central aperture formed through the rotor and (b) passing a second portion of the flow of blood through a gap formed between the rotor and the housing.

In many embodiments, the method further includes magnetically levitating the rotor within the blood flow channel. For example, the rotor can be levitated within the blood flow channel such that the rotor is separated from the housing by a gap between about 0.2 mm to about 2 mm. The rotor can be levitated within the blood flow channel such that the rotor is separated from at least one of the stator coils by a gap between about 0.3 mm to about 2.4 mm.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
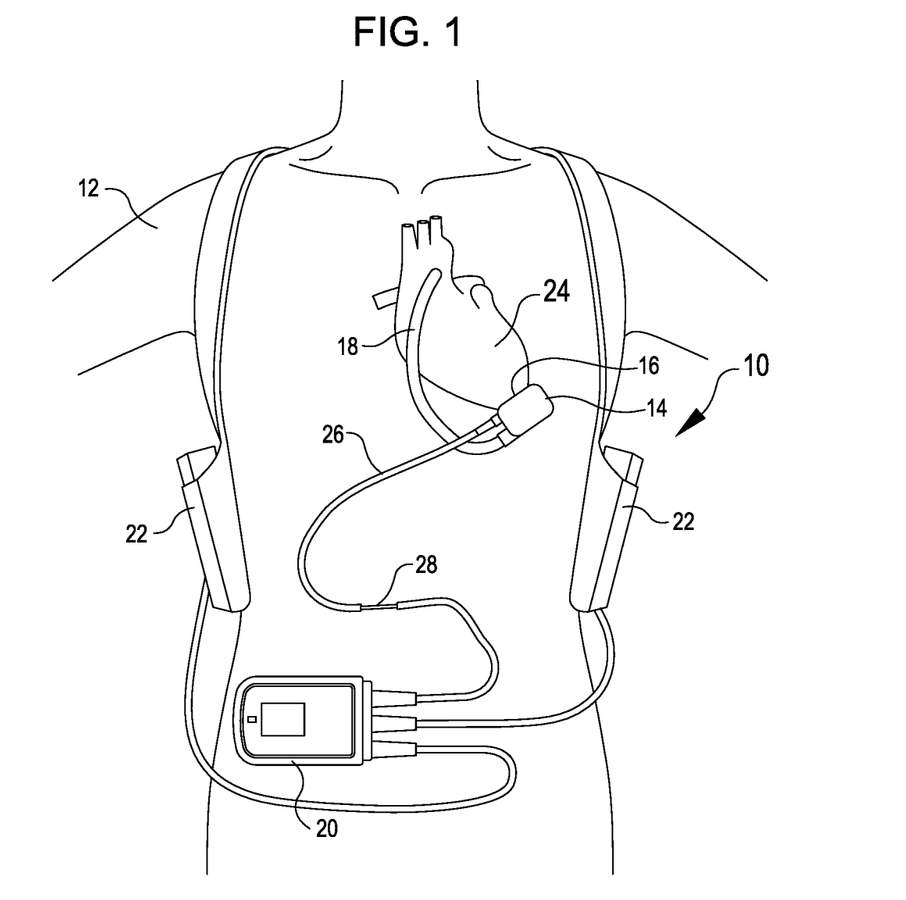
FIG. 1 is an illustration of a mechanical circulatory support system implanted in a patient's body, in accordance with many embodiments.

Referring now to the drawings, in which like reference numerals represent like parts throughout the several views, FIG. 1 shows a mechanical circulatory support system 10 implanted in a patient's body 12. The mechanical circulatory support system 10 includes an implantable blood pump assembly 14, a ventricular cuff 16, an outflow cannula 18, an external system controller 20, and power sources 22. The implantable blood pump assembly 14 can include a VAD that is attached to an apex of the left ventricle, as illustrated, or the right ventricle. A respective VAD can be attached to each of the ventricles of the heart 24. The VAD can include a centrifugal pump (as shown) that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,976,271, 7,997,854, 8,007,254, 8,152,493, 8,419,609, 8,852,072, 8,652,024, 8,668,473, 8,864,643, 8,882,744, 9,068,572, 9,091,271, 9,265,870, and 9,382,908, all of which are incorporated herein by reference for all purposes in their entirety. The blood pump assembly 14 can be attached to the heart 24 via the ventricular cuff 16, which can be sewn to the heart 24 and coupled to the blood pump 14. The other end of the blood pump 14 connects to the ascending aorta (or the pulmonary artery when the VAD is coupled with the right ventricle of the heart) via the outflow cannula 18 so that the VAD effectively diverts blood from the weakened ventricle and propels it for circulation through the patient's vascular system.

FIG. 1 illustrates the mechanical circulatory support system 10 during battery 22 powered operation. A driveline 26 that exits through the patient's abdomen 28 connects the implanted blood pump assembly 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system 10 can be powered by either one, two, or more batteries 22. It will be appreciated that although the system controller 20 and power source 22 are illustrated outside/external to the patient body, the driveline 26, the system controller 20 and/or the power source 22 can be partially or fully implantable within the patient, as separate components or integrated with the blood pump assembly 14. Examples of such modifications are further described in U.S. Pat. Nos. 8,562,508 and 9,079,043, all of which are incorporated herein by reference for all purposes in their entirety.

Figure 2:
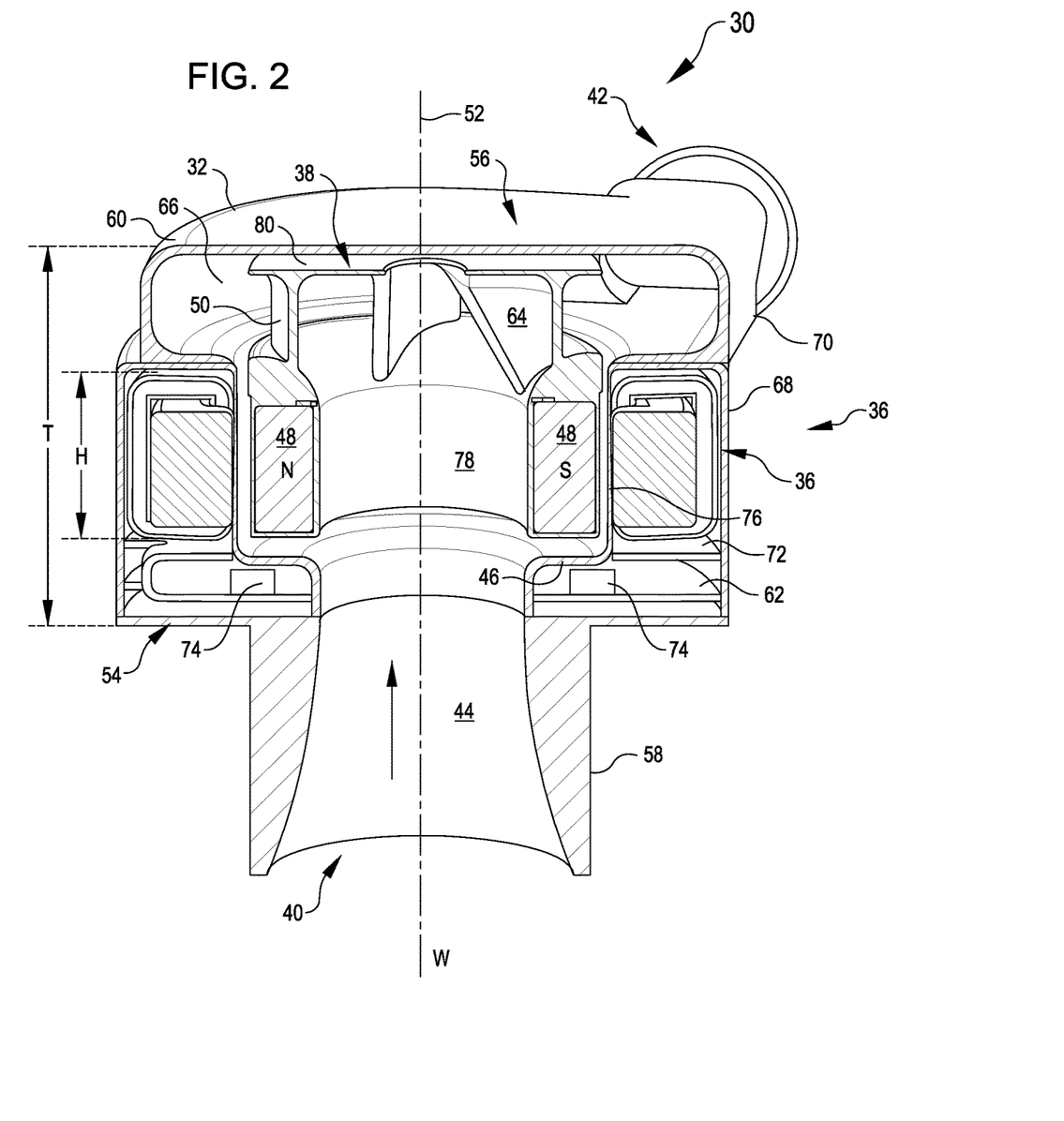
FIG. 2 is a cross-sectional view illustration of an implantable blood pump that includes a compact rotary motor that includes a toroidal stator core with teeth, in accordance with some embodiments.

FIG. 2 is a cross-sectional view illustration of an implantable blood pump assembly 30, in accordance with some embodiments. The blood pump assembly 30 can be used in place of the blood pump assembly 14 in the mechanical circulatory support system 10. The blood pump assembly 30 includes a housing 32 and a compact rotary motor 34. The compact rotary motor 34 includes a stator 36 and a rotor assembly 38. The housing 32 defines an inlet opening 40, an outlet opening 42, and a blood flow conduit 44 in fluid communication with the inlet opening 40 and the outlet opening 42. The housing 32 includes a dividing wall 46 that defines the blood flow conduit 44. The dividing wall 46 also partially defines a compartment in which the stator 36 is disposed and isolates the stator from blood flowing through the blood flow conduit 44. The rotor assembly 38 includes a rotor magnetic assembly 48 and an impeller blade assembly 50 attached to the rotor magnetic assembly 48. The rotor magnetic assembly 48 can include any suitable number of permanent magnets (e.g., 1 or more). In operation, the stator 36 generates magnetic fields that interact with the rotor magnetic assembly 48 to levitate the rotor magnetic assembly 48 radially within the blood flow conduit 44, rotate the rotor magnetic assembly 48 within the blood flow conduit 44 around a rotor axis of rotation 52, and react axial thrust applied to the rotor assembly 38 parallel to the rotor axis of rotation 52 during pumping of blood through the blood flow conduit 44 via rotation of the rotor assembly 38.

The housing 32 has a circular shape and is implanted in a patient's body with a first face 54 of the housing 32 facing the patient's heart 24 and a second face 56 of the housing 32 facing away from the heart 24. The housing 32 includes an inlet cannula 58 that couples with the ventricular cuff 16 and extends into a ventricle of the heart 24. The second face 56 of the housing 32 has a chamfered edge 60 to avoid irritating other tissue that may come into contact with the blood pump assembly 30, such as the patient's diaphragm. To construct the illustrated shape of the puck-shaped housing 32 in a compact form, the stator 36 and electronics 62 of the pump assembly 30 are positioned on the inflow side of the housing 32 toward first face 54, and the rotor assembly 38 is positioned along the second face 56. This positioning of the stator 36, electronics 62, and the rotor assembly 38 permits the edge 60 to be chamfered along the contour of the impeller blade assembly 50.

The blood flow conduit 44 extends from the inlet opening 40 of the inlet cannula 58 through the stator 36 to the outlet opening 42. The rotor assembly 38 is positioned within the blood flow conduit 44. The stator 36 is disposed circumferentially around the rotor magnetic assembly 48. The stator 36 is also positioned relative to the rotor assembly 38 such that, in use, blood flows within the blood flow conduit 44 through the stator 36 and the rotor magnetic assembly 48 before reaching the impeller blade assembly 50. In some embodiments, the rotor magnetic assembly 48 has a permanent magnetic north pole (N) and a permanent magnetic south pole (S) for combined active and passive magnetic levitation of the rotor magnetic assembly 48 and for rotation of the rotor assembly 38. In some embodiments, the rotor magnetic assembly 48 has more than one pair of magnetic poles (e.g., 2, 3, 4, 5, or more). The impeller blade assembly 50 includes impeller blades 64. The impeller blades 64 are located within a volute 66 of the blood flow conduit 44 such that the impeller blades 64 are located proximate to the second face 56 of the housing 32.

The puck-shaped housing 32 further includes a peripheral wall 68 that extends between the first face 54 and a removable cap 70. As illustrated, the peripheral wall 68 is formed as a hollow circular cylinder having a width (W) between opposing portions of the peripheral wall 68. The housing 32 also has a thickness (T) between the first face 54 and the second face 56 that is less than the width (W). The thickness (T) is from about 0.5 inches to about 1.5 inches, and the width (W) is from about 1 inch to about 4 inches. For example, the width (W) can be approximately 2 inches, and the thickness (T) can be approximately 1 inch.

The peripheral wall 68 encloses an internal compartment 72 that surrounds the dividing wall 46 and the blood flow conduit 44, with the stator 36 and the electronics 62 disposed in the internal compartment 72 about the dividing wall 46. The removable cap 70 includes the second face 56, the chamfered edge 60, and defines the outlet opening 42. The cap 70 has an inner surface that defines the volute 66 that is in fluid communication with the outlet opening 42.

Within the internal compartment 72, the electronics 62 are positioned adjacent to the first face 54 and the stator 36 is positioned adjacent to the electronics 62 on an opposite side of the electronics 62 from the first face 54. The electronics 62 can include one or more circuit boards and various components carried on the circuit boards to control the operation of the blood pump assembly 30 (e.g., magnetic levitation and/or drive of the rotor assembly 38) by controlling currents applied to the stator 36. The housing 32 is configured to receive the electronics 62 within the internal compartment 72 generally parallel to the first face 54 for efficient use of the space within the internal compartment 72. The electronics 62 also extend radially-inward towards the dividing wall 46 and radially-outward towards the peripheral wall 68. For example, the internal compartment 72 is generally sized no larger than necessary to accommodate the stator 36 and the electronics 62, and space for heat dissipation, material expansion, potting materials, and/or other elements used in installing the stator 36 and the electronics 62. Thus, the external shape of the housing 32 proximate the first face 54 generally fits the shape of the electronics 62 closely to provide external dimensions that are not much greater than the dimensions of the electronics 62. In the illustrated embodiment, the electronics 62 include Hall effect sensors 74 that generate output indicative of the angular orientation of the rotor magnetic assembly 48 and the transverse position of the rotor magnetic assembly 48 transverse to the rotor axis of rotation 52 in two directions. The output from the Hall effect sensors 74 is used by the electronics 62 to control operation of the stator 36 to levitate and rotate the rotor assembly 38.

The rotor assembly 38 is arranged within the housing 32 such that the rotor magnetic assembly 48 is located upstream of the impeller blade assembly 50. The rotor magnetic assembly 48 is disposed within the blood flow conduit 44 proximate the stator 36. The rotor magnetic assembly 48 and the dividing wall 44 form a gap 76 between the rotor magnetic assembly 48 and the dividing wall 44 when the rotor magnetic assembly 48 is centered within the blood flow conduit 44. In many embodiments, the gap 76 is from about 0.2 millimeters to about 2 millimeters. In some embodiments, the gap 76 is approximately 1 millimeter. The north permanent magnetic pole N and the south permanent magnetic pole S of the rotor magnetic assembly 48 provide a permanent magnetic attractive force between the rotor magnetic assembly 48 and the stator 36 that acts as a passive axial force that tends to maintain the rotor magnetic assembly 48 generally axially aligned with the stator 36 relative to the rotor axis of rotation 52 thereby resisting movement of the rotor magnetic assembly 48 towards the first face 54 or towards the second face 56.

As blood flows through the blood flow conduit 44, blood flows through a central aperture 78 formed through the rotor magnetic assembly 48. Blood also flows through the gap 76 between the rotor magnetic assembly 48 and the dividing wall 46 and through a gap 80 between the impeller blade assembly 50 and the inner surface of the cap 70. The gaps 76 and 80 are large enough to allow adequate blood flow to limit clot formation that may occur if the blood is allowed to become stagnant. The gaps 76 and 80 are also large enough to limit shear forces on the blood cells such that the blood is not damaged when flowing through the blood pump assembly 30. As a result of the size of the gaps 76 and 80 limiting shear forces on the blood cells, the gaps 76 and 80 are too large to provide a meaningful hydrodynamic suspension effect. That is to say, the blood does not act as a bearing within the gaps 76 and 80, and the rotor magnetic assembly 48 is only magnetically-levitated.

Because the rotor assembly 38 is radially suspended by active control of the stator 36, and because the rotor assembly 38 is axially suspended by passive interaction between the stator 36 and the rotor magnetic assembly 48, no rotor levitation components other than the stator 36 and related components used to control operation of the stator 36 are needed (e.g., proximate the second face 56) to levitate the rotor assembly 38 transverse to the rotor axis of rotation 52 and to control the position of the rotor assembly 38 parallel to the rotor axis of rotation 52. By levitating the rotor assembly 38 via the stator 36, the cap 70 can be contoured to the shape of the impeller blade assembly 50 and the volute 66. Additionally, levitating the rotor assembly 38 via the stator 36 eliminates the need for electrical connectors extending from the compartment 72 to the cap 70, which allows the cap 70 to be easily installed and/or removed and eliminates potential sources of pump failure.

Figure 3:
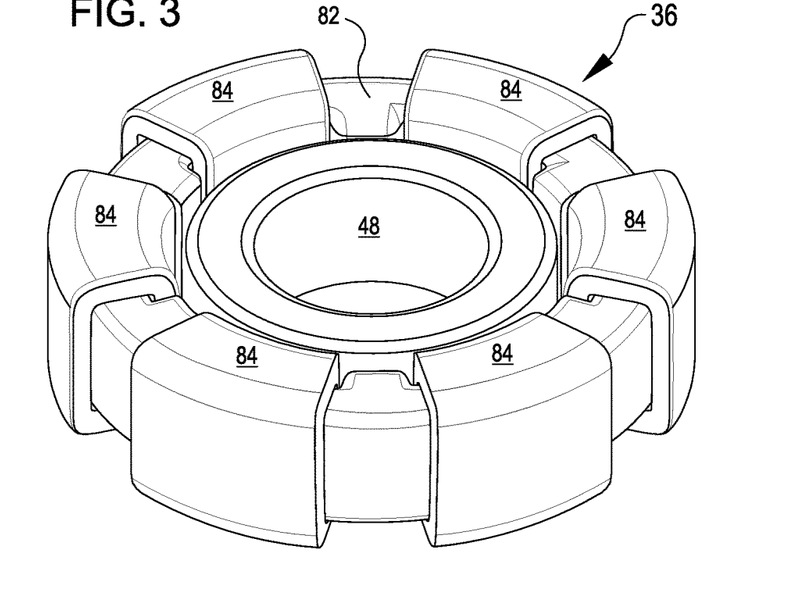
FIG. 3 is an isometric view illustration of the stator core and a rotor component of the compact rotary motor of FIG. 2.
Figure 4:
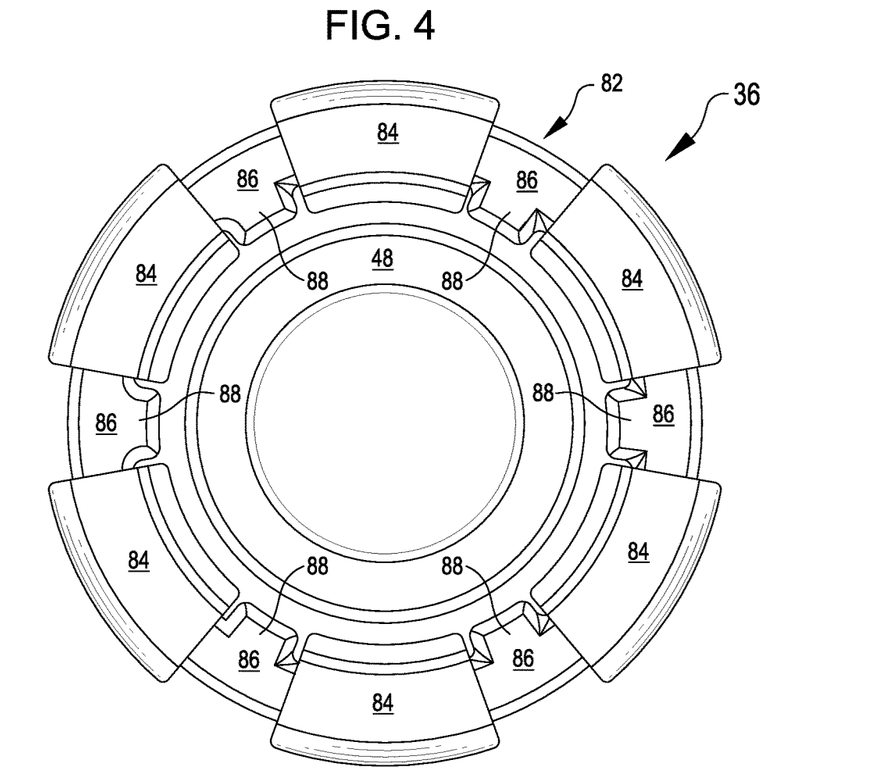
FIG. 4 is an axial view illustration of the stator core and a rotor component of the compact rotary motor of FIG. 2.

FIG. 3 and FIG. 4 show the stator 36 and the rotor magnetic assembly 48. The stator 36 includes an integral stator core 82 and stator coils 84. The integral stator core 82 includes a toroidal portion 86 and stator teeth 88. Each of the stator teeth 88 extends toward the rotor magnetic assembly 48 from the toroidal portion 86. Each of the stator teeth 88 is separated from each of an adjacent two of the stator teeth 88 by a respective adjacent intervening segment of the toroidal portion 86. Each of the stator coils 84 extends around one of the intervening segments of the toroidal portion 86. The stator 36 is disposed within the housing 32 circumferentially around the dividing wall 46 such that the blood flow conduit 44 extends through the stator core 82. The stator core 82 is disposed circumferentially around the rotor magnetic assembly 48. In many embodiments, the stator 36 does not extend beyond a disk-shaped volume having a compact thickness (e.g., (H) shown in FIG. 2 less than 1.0 inches) in a direction parallel to the rotor axis of rotation 52.

Figure 5:
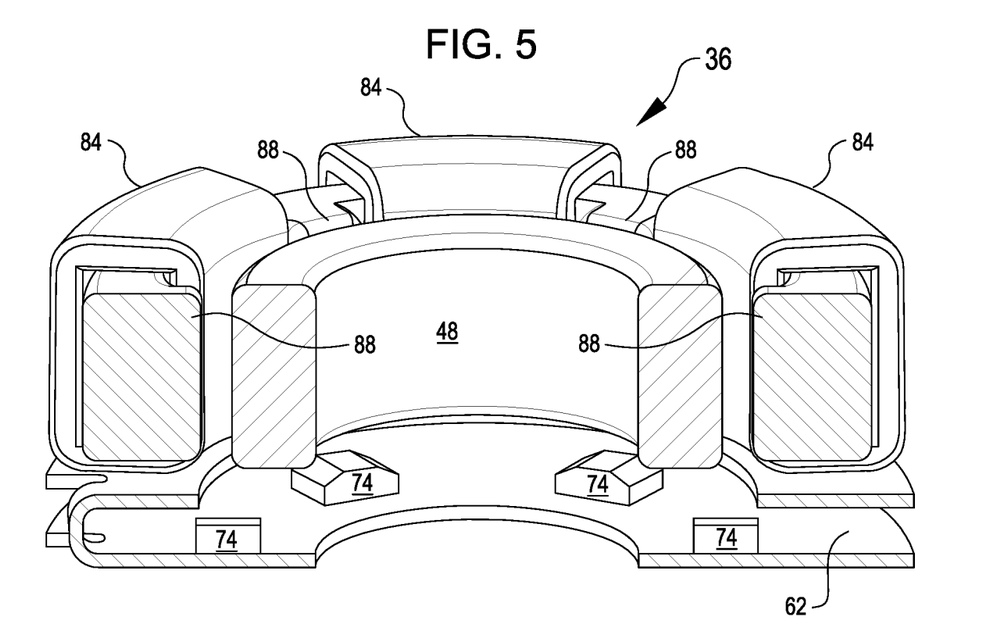
FIG. 5 is a cross-sectional view illustration of the stator core, the rotor component, and rotor position sensors of the compact rotary motor of FIG. 2.

FIG. 5 is a cross-sectional view illustration of the stator 36, the rotor magnetic assembly 48, and the electronics 62. In the illustrated embodiment, the electronics 62 include Hall-effect sensors 74, each of which is disposed adjacent to a respective one of the stator teeth 88. By positioning the Hall-effect sensors 74 aligned with the stator teeth 88, the signals generated by the Hall-effect sensors 74 can be processed to track the orientation of the rotor magnetic assembly 48 relative to the stator teeth 88 without adjusting for an orientation difference between the Hall-effect sensors 74 and the stator teeth 88.

Figure 6:
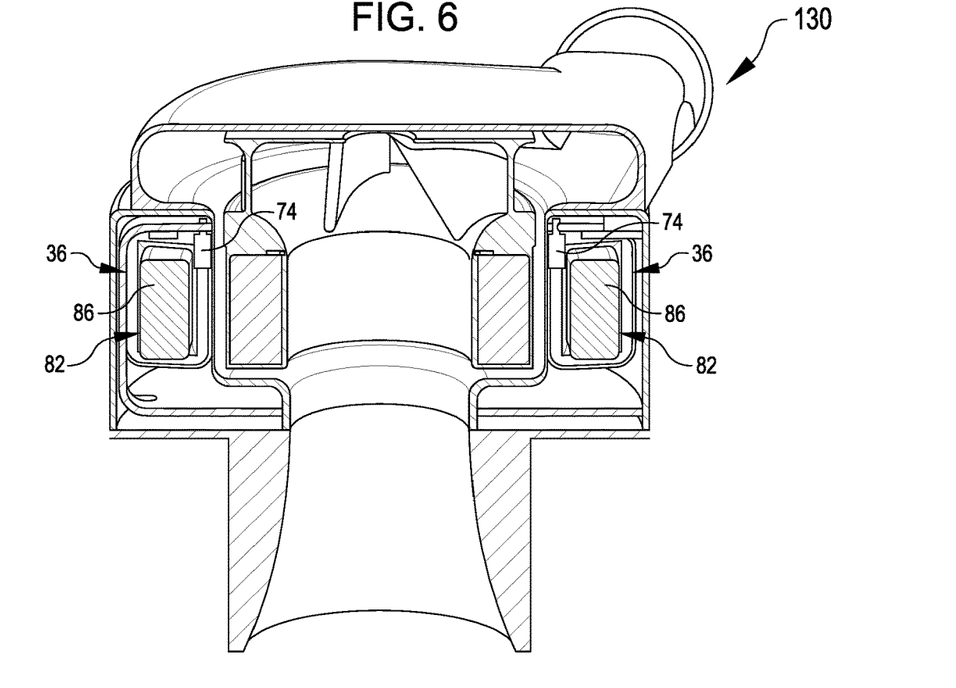
FIG. 6 is a cross-sectional view illustration of an implantable blood pump that includes a compact rotary motor that includes a toroidal stator core without teeth, in accordance with some embodiments.
Figure 7:
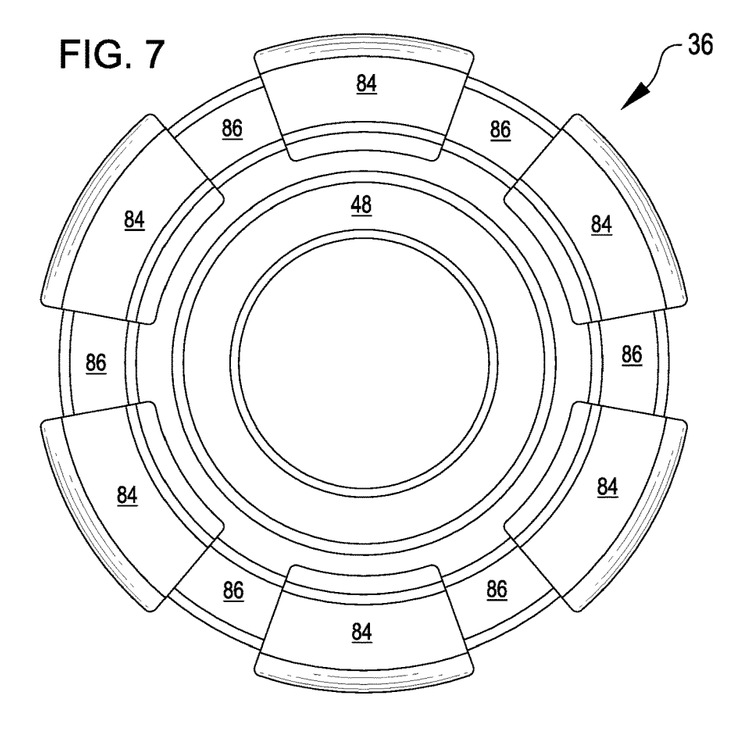
FIG. 7 is an axial view illustration of the stator core and a rotor component of the compact rotary motor of FIG. 6.
Figure 8:
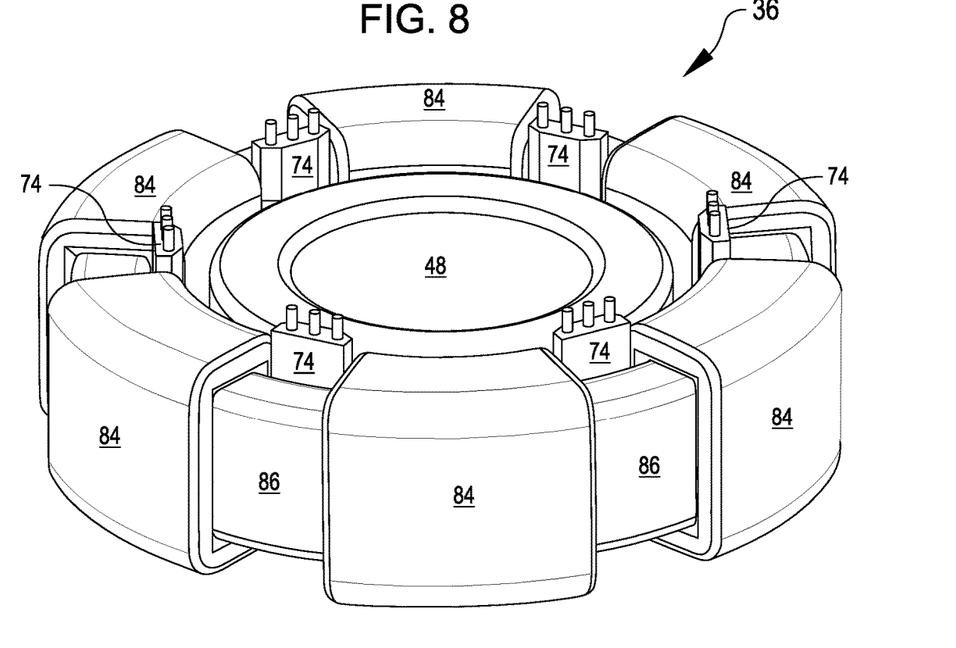
FIG. 8 is an isometric view illustration of the stator core, the rotor component, and hall effect sensors of the compact rotary motor of FIG. 6.
Figure 9:
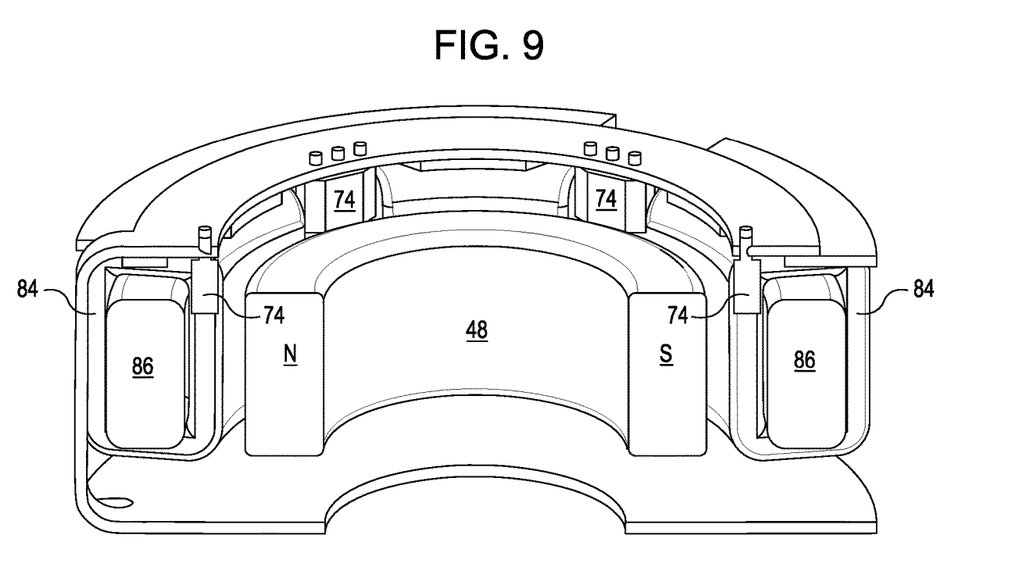
FIG. 9 is a cross-sectional view illustration of the stator core, the rotor component, and hall effect sensors of the compact rotary motor of FIG. 6.

FIG. 6 is a cross-sectional view illustration of an implantable blood pump assembly 130, in accordance with some embodiments. The blood pump assembly 130 can be used in place of the blood pump assembly 14 in the mechanical circulatory support system 10. The blood pump assembly 130 is configured similar to the blood pump assembly 30 except for differences with respect to the stator core 82 and the location of the Hall-effect sensors 74 as described herein. Accordingly, components of the blood pump assembly 130 that are the same or similar to the components of the blood pump assembly 30 are identified using the same or similar reference identifiers in the drawing figures. As illustrated in FIG. 6 and FIG. 7, the stator core 82 of the blood pump assembly 130 includes the toroidal portion 86 and does not include the stator teeth 88 of the stator core 82 of the blood pump assembly 30. As illustrated in FIG. 6, FIG. 8, and FIG. 9, each of the Hall-effect sensors 74 in the blood pump assembly 130 is located in a respective gap between adjacent stator coils 86 that corresponds to a space that is occupied by a respective stator tooth 88 in the blood pump assembly 30.

Figure 10:
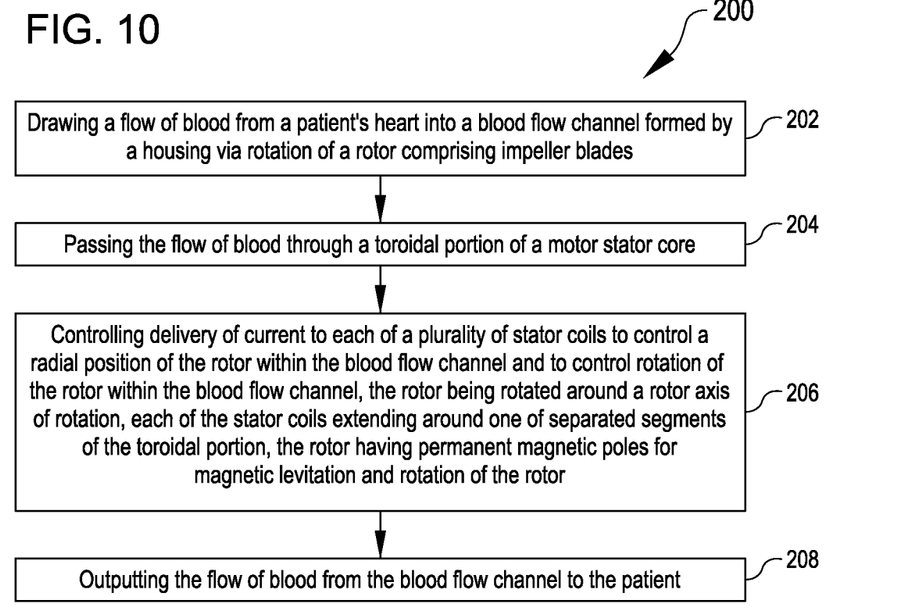
FIG. 10 is a simplified schematic diagram illustration of a method of assisting blood circulation in a patient, in accordance with many embodiments.

FIG. 10 is a simplified schematic diagram illustration of a method 200 of assisting blood circulation in a patient, in accordance with many embodiments. Any suitable blood pump assembly, such as the blood pump assemblies 14, 30, 130 described herein, can be used to practice the method 200.

The method 200 includes drawing a flow of blood from a patient's heart into a blood flow channel formed by a housing via rotation of a rotor comprising impeller blades (act 202). For example, with reference to FIG. 2, the rotor assembly 38 can be levitated and rotated via application of drive currents to the stator 36, thereby drawing blood from the patient's ventricle into the inlet cannula 58 and pumping the blood through the blood flow conduit 44.

The method 200 includes passing the flow of blood through a toroidal portion of a motor stator core (act 204). For example, with reference to FIG. 2 and FIG. 4, the flow of blood passes through the toroidal portion 86 of the motor stator core 82 as the blood flows through the blood flow conduit 44.

The method 200 includes controlling delivery of current to each of a plurality of stator coils to control a radial position of the rotor within the blood flow channel and to control rotation of the rotor within the blood flow channel, the rotor being rotated around a rotor axis of rotation, each of the stator coils extending around one of separated segments of the toroidal portion, the rotor having permanent magnetic poles for magnetic levitation and rotation of the rotor (act 206). For example, with reference to FIG. 2 through FIG. 4, delivery of current to each of the stator coils 84 is controlled (e.g., via the electronics 62) to control a radial position of the rotor magnetic assembly 48 within the blood flow conduit 44 (i.e., transverse to the rotor axis of rotation 52) and to control rotation of the rotor magnetic assembly 48 within the blood flow conduit 44. The rotor magnetic assembly 48 is rotated around the rotor axis of rotation 52. Each of the stator coils 84 extends around one of separated segments of the toroidal portion 86. The rotor magnetic assembly 48 has permanent magnetic poles for magnetic levitation and rotation of the rotor magnetic assembly 48.

The method 200 includes outputting the flow of blood from the blood flow channel to the patient (act 208). For example, referring to FIG. 2, the blood flowing through the blood flow conduit 44 is output via the outlet opening 42 and to the ascending aorta via the outflow cannula 18.

Figure 11:
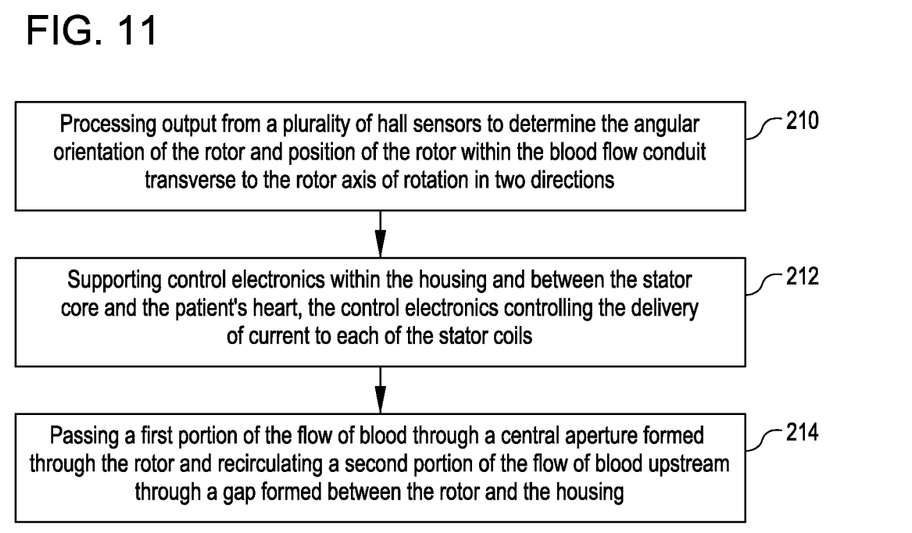
FIG. 11 is a simplified schematic diagram illustration of additional acts that can be accomplished in the method of FIG. 10.

FIG. 11 is a simplified schematic diagram illustration of additional acts that can be accomplished in the method 200. For example, the method 200 can further include processing output from a plurality of Hall-effect sensors to determine the angular orientation of the rotor and the position of the rotor transverse to the rotor axis of rotation in two directions (act 210). Each of the Hall-effect sensors can be aligned with a respective gap between an adjacent pair of the stator coils (e.g., above the respective gap, below the respective gap, in the respective gap). For example, referring to FIG. 6, FIG. 8, and FIG. 9, output from the Hall-effect sensors 74 is processed (e.g., via the electronics 62) to determine the orientation of the rotor magnetic assembly 48 for use in controlling supply of current to each of the stator coils 84 to control levitation and rotation of the rotor magnetic assembly 48. In the blood pump assembly 130, each of the Hall-effect sensors 74 is disposed in a respective gap between an adjacent pair of the stator coils 84.

Method 200 can further include supporting control electronics within the housing and between the stator core and the patient's heart, the control electronics controlling the delivery of current to each of the stator coils (act 212). For example, referring to FIG. 2, the electronics 62 are supported within the housing 32 and control delivery of current to each of the stator coils 84.

Method 200 can further include passing a first portion of the flow of blood through a central aperture formed through the rotor and passing a second portion of the flow of blood through a gap formed between the rotor and the housing (act 214). For example, referring to FIG. 2, a first portion of the blood flowing through the blood flow conduit 44 passes through a central aperture formed through the rotor magnetic assembly 48 and a second portion of the blood flowing through the blood flow conduit 44 recirculates back upstream through the gaps 76, 80 formed between the rotor assembly 38 and the housing 32.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An implantable blood pump comprising:
    a housing defining an inlet opening, an outlet opening, and a dividing wall within the housing defining a blood flow passage that extends between the inlet opening and the outlet opening;
    a rotary motor including a stator and a rotor; wherein the stator comprises a stator core and stator coils, wherein the stator core has a toroidally-shaped external surface that extends circumferentially and continuously around an axis of rotation of the rotor, wherein each of the stator coils is wound around and encloses a respective circumferentially extending segment of the toroidally-shaped external surface, wherein each of the stator coils is separated from each of two adjacent instances of the stator coils by an intervening gap that corresponds to a respective exposed circumferentially extending segment of the toroidally-shaped external surface, wherein the stator is disposed within the housing circumferentially about the dividing wall such that the blood flow passage extends through the stator core, wherein the stator core is disposed circumferentially around at least a portion of the rotor, wherein the rotor includes a rotor magnet for driving the rotor, and wherein the stator core overlaps the rotor magnet with respect to the axis of rotation of the rotor; and
    control electronics disposed within the housing and configured to control current passing through each of the stator coils to radially levitate the rotor and rotate the rotor within the blood flow passage.

2. The implantable blood pump of claim 1, wherein the outlet opening is oriented at an angle relative to the inlet opening.

3. The implantable blood pump of claim 1, wherein the rotor comprises centrifugal pump impeller blades.

4. The implantable blood pump of claim 3, wherein the rotor defines a rotor blood flow passage extending through the rotor.

5. The implantable blood pump of claim 1, wherein the rotor defines a rotor blood flow passage extending through the rotor.

6. The implantable blood pump of claim 1, wherein the rotor has only one magnetic moment.

7. The implantable blood pump of claim 1, wherein an axial position of the rotor along the blood flow passage is restrained via passive magnetic interaction between the rotor and the stator.

8. The implantable blood pump of claim 1, wherein the rotor and the dividing wall are separated by a distance in a range from 0.2 mm to 2 mm with the rotor centered relative to the stator core.

9. The implantable blood pump of claim 1, wherein the rotor and at least one of the stator coils are separated by a distance in a range from 0.3 mm to 2.4 mm with the rotor centered relative to the stator core.

10. The implantable blood pump of claim 1, further comprising hall effect sensors for monitoring an orientation and one or more positions of the rotor relative to the stator.

11. A ventricular assist device comprising:
    a housing defining an inlet opening, an outlet opening, and a dividing wall within the housing defining a blood flow passage that extends between the inlet opening and the outlet opening;
    a rotary motor including a stator and a rotor; wherein the stator is operable to rotate the rotor around a rotor around a rotor axis of rotation, wherein the stator comprises a stator core and stator coils, wherein the stator core has a toroidally-shaped external surface that extends circumferentially and continuously around the rotor axis of rotation, wherein each of the stator coils is wound around and encloses a respective circumferentially extending segment of the toroidally-shaped external surface, wherein each of the stator coils is separated from each of two adjacent instances of the stator coils by an intervening gap that corresponds to a respective exposed circumferentially extending segment of the toroidally-shaped external surface, wherein the stator does not extend beyond a disk-shaped volume having a thickness in a direction parallel to the rotor axis of rotation of less than 1.0 inches, wherein the stator is disposed within the housing circumferentially about the dividing wall such that the blood flow passage extends through the stator core, wherein the stator core is disposed circumferentially around at least a portion of the rotor, wherein the rotor includes a rotor magnet for driving the rotor, and wherein the stator core axially overlaps the rotor magnet with respect to the rotor axis of rotation; and control electronics disposed within the housing and configured to control current supplied to the stator to radially levitate the rotor and rotate the rotor within the blood flow passage.

12. The ventricular assist device of claim 11, wherein:

a housing comprising an inlet cannula and a first side face from which the inlet cannula extends;

the inlet cannula is configured to couple with a ventricular cuff attached to a heart and extend into a ventricle of the heart; and the housing extends by a maximum distance of 1.5 inches from the first side face in a direction away from the inlet cannula.

13. The ventricular assist device of claim 11, wherein the outlet opening is oriented at an angle relative to the inlet opening.

14. The ventricular assist device of claim 11, wherein the rotor comprises centrifugal pump impeller blades.

15. The ventricular assist device of claim 14, wherein the rotor defines a rotor blood flow passage extending through the rotor.

16. The ventricular assist device of claim 11, wherein the rotor defines a rotor blood flow passage extending through the rotor.

17. The ventricular assist device of claim 11, wherein the rotor has only one magnetic moment.

18. The ventricular assist device of claim 11, wherein an axial position of the rotor along the blood flow passage is restrained via passive magnetic interaction between the rotor and the stator.

19. The ventricular assist device of claim 11, wherein the rotor and the dividing wall are separated by a distance in a range from 0.2 mm to 2 mm with the rotor centered relative to the stator core.

20. The ventricular assist device of claim 11, wherein the rotor and the stator are separated by a distance in a range from 0.3 mm to 2.4 mm with the rotor centered relative to the stator core.

21. The ventricular assist device of claim 11, further comprising hall effect sensors for monitoring an orientation and one or more positions of the rotor relative to the stator.

* * * * *